United States Patent
Hidaka

(10) Patent No.: US 10,571,417 B2
(45) Date of Patent: Feb. 25, 2020

(54) ELECTRICAL CHARACTERISTIC MEASUREMENT APPARATUS, ELECTRICAL CHARACTERISTIC MEASUREMENT SYSTEM, ELECTRICAL CHARACTERISTIC MEASUREMENT METHOD, AND PROGRAM FOR ELECTRICAL CHARACTERISTIC MEASUREMENT FOR CAUSING COMPUTER TO IMPLEMENT THE METHOD

(71) Applicant: Sony Corporation, Tokyo (JP)

(72) Inventor: Isao Hidaka, Tokyo (JP)

(73) Assignee: Sony Corporation, Tokyo (JP)

( * ) Notice: Subject to any disclaimer, the term of this patent is extended or adjusted under 35 U.S.C. 154(b) by 147 days.

(21) Appl. No.: 15/550,192

(22) PCT Filed: Jan. 14, 2016

(86) PCT No.: PCT/JP2016/050911
§ 371 (c)(1),
(2) Date: Aug. 10, 2017

(87) PCT Pub. No.: WO2016/132779
PCT Pub. Date: Aug. 25, 2016

(65) Prior Publication Data
US 2018/0031503 A1    Feb. 1, 2018

(30) Foreign Application Priority Data
Feb. 20, 2015  (JP) .................. 2015-032176

(51) Int. Cl.
*G01N 27/02*  (2006.01)
*G01N 33/487*  (2006.01)
(Continued)

(52) U.S. Cl.
CPC ..... *G01N 27/028* (2013.01); *G01N 33/48707* (2013.01); *G01N 33/4905* (2013.01); *G01N 27/021* (2013.01); *G01N 33/86* (2013.01)

(58) Field of Classification Search
CPC .... G01N 27/02; G01N 27/021; G01N 27/028; G01N 27/04; G01N 27/045; G01N 27/22;
(Continued)

(56) References Cited

U.S. PATENT DOCUMENTS

2010/0305499 A1* 12/2010 Matsiev ............... A61B 5/145
                                                        604/67
2012/0035450 A1    2/2012 Hayashi
(Continued)

FOREIGN PATENT DOCUMENTS

CN  1543912 A    11/2004
CN  102667476 A   9/2012
(Continued)

OTHER PUBLICATIONS

International Search Report and Written Opinion and English translation thereof dated Mar. 29, 2016 in connection with International Application No. PCT/JP2016/050911.
(Continued)

*Primary Examiner* — Maureen Wallenhorst
(74) *Attorney, Agent, or Firm* — Wolf, Greenfield & Sacks, P.C.

(57) ABSTRACT

A technology is provided that enables high accuracy electrical measurement regardless of the performance of a measurement device. An electrical characteristic measurement apparatus includes a measurement unit that measures an electrical characteristic of a biological sample in a plurality of frequencies; and an assignment unit that performs assignment of a number of measurements and/or a measurement amplitude for each frequency. Use of a com-
(Continued)

bination of a frequency for which the signal-to-noise ratio (SNR) is intentionally left low and a frequency for which the SNR is on the contrary improved when an electrical characteristic of a biological sample is measured in multiple frequencies, can provide, as a result, high accuracy electrical measurement optimal for the purpose of measurement.

12 Claims, 5 Drawing Sheets

(51) Int. Cl.
 *G01N 33/49* (2006.01)
 *G01N 33/86* (2006.01)
(58) Field of Classification Search
 CPC ............... G01N 27/228; G01N 33/487; G01N 33/48707; G01N 33/49; G01N 33/4905; G01N 33/86
 USPC ........... 436/63, 69, 149, 150; 422/73, 82.01, 422/82.02; 435/13
 See application file for complete search history.

(56) References Cited

U.S. PATENT DOCUMENTS

| | | |
|---|---|---|
| 2012/0105075 A1 | 5/2012 | Phlippoteau et al. |
| 2012/0232803 A1 | 9/2012 | Viola et al. |
| 2015/0323480 A1 | 11/2015 | Brun et al. |

FOREIGN PATENT DOCUMENTS

| | | | |
|---|---|---|---|
| CN | 102687008 A | | 9/2012 |
| CN | 104204787 A | | 12/2014 |
| EP | 2375244 | * | 10/2011 |
| EP | 2375244 A1 | | 10/2011 |
| EP | 2950087 A1 | | 12/2015 |
| JP | 64-088376 A | | 4/1989 |
| JP | 05-209912 A | | 8/1993 |
| JP | 11-352162 A | | 12/1999 |
| JP | 2009-042141 A | | 2/2009 |
| JP | 2010-181400 A | | 8/2010 |
| JP | 2012-518797 A | | 8/2012 |
| WO | WO 2014/115478 A1 | | 7/2014 |

OTHER PUBLICATIONS

International Preliminary Report on Patentability and English translation thereof dated Aug. 31, 2017 in connection with International Application No. PCT/JP2016/050911.

Extended European Search Report dated Oct. 5, 2018 in connection with European Application No. 16752168.1.

Chinese Office Action dated May 13, 2019 in connection with Chinese Application No. 2016800096603, and English translation thereof.

* cited by examiner

PRIOR ART

ELECTRICAL CHARACTERISTIC MEASUREMENT APPARATUS, ELECTRICAL CHARACTERISTIC MEASUREMENT SYSTEM, ELECTRICAL CHARACTERISTIC MEASUREMENT METHOD, AND PROGRAM FOR ELECTRICAL CHARACTERISTIC MEASUREMENT FOR CAUSING COMPUTER TO IMPLEMENT THE METHOD

CROSS-REFERENCE TO RELATED APPLICATIONS

This application claims the benefit under 35 U.S.C. § 371 as a U.S. National Stage Entry of International Application No. PCT/JP2016/050911, filed in the Japanese Patent Office as a Receiving Office on Jan. 14, 2016, which claims priority to Japanese Patent Application Number JP 2015-032176, filed in the Japanese Patent Office on Feb. 20, 2015, each of which is hereby incorporated by reference in its entirety.

TECHNICAL FIELD

The present technology relates to an electrical characteristic measurement apparatus, and more particularly, to an apparatus, an electrical characteristic measurement system, and an electrical characteristic measurement method, each for measuring an electrical characteristic of a biological sample in multiple frequencies, as well as to a program for causing a computer to implement the method.

BACKGROUND ART

Techniques have been performed that measure an electrical characteristic of a sample, and determine a physical property of the sample from the measurement result, and/or determine the type of cells and/or the like contained in the sample (see, e.g., Patent Document 1). Examples of electrical characteristic measured include a complex permittivity and its frequency dispersion (dielectric spectrum). A complex permittivity and its frequency dispersion are typically calculated by applying an electrical voltage (hereinafter referred to simply as "voltage") to the sample solution, and then measuring a complex capacitance or a complex impedance across electrodes.

In addition, for example, Patent Document 2 discloses a technology for obtaining information relating to blood coagulation from an electrical permittivity (hereinafter referred to simply as "permittivity") of the blood, and describes "a blood coagulation system analysis device including: a pair of electrodes; application means for applying an alternating voltage to the pair of electrodes at predetermined time intervals; measurement means for measuring a permittivity of blood which is positioned between the pair of electrodes; and analysis means for analyzing a degree of the action of a blood coagulation system by using the permittivity of blood which is measured at the time intervals after the anticoagulant effect acting on the blood is ended."

Electrical measurement of a biological sample such as one described above typically uses a method that obtains a state of the biological sample by applying a signal in multiple frequency bands to the biological sample, and receiving a response therefor. Response acquisition methods using multiple frequencies include a method that divides time for acquiring a response for a single frequency band (time-division method), and a method that acquires a response by synthesizing an application signal at one time (frequency-multiplexing method).

An example of time-division method is illustrated in FIG. 8. In this example, a response is acquired in three frequencies, which are 100 kHz, 1 MHz, and 10 MHz, in each measurement, and eight measurements are performed at each frequency. Thus, the measurement in each frequency is performed such that multiple measurements are performed at time intervals, and the measured values are then averaged to cancel out variation between measurements. The signal-to-noise ratio (SNR) is thus improved.

An example of frequency-multiplexing method is illustrated in FIG. 9. In this example, a method is used in which signals having a same amplitude and respectively having frequencies of 100 kHz, 1 MHz, and 10 MHz (three signals in the lower part of the diagram) are superimposed; the superimposed signal (the topmost signal in the diagram) is obtained; and this signal is then applied to the analyte to obtain a response. During the measurements, similarly to the time-division multiplexing described above, multiple measurements are performed, and the measured values are then averaged to cancel out variation between measurements. The SNR is thus improved. This example illustrates an example of performing 24 measurements during the entire time span (in FIG. 9, one second).

CITATION LIST

Patent Document

Patent Document 1: Japanese Patent Application Laid-Open No. 2009-042141
Patent Document 2: Japanese Patent Application Laid-Open No. 2010-181400

SUMMARY OF THE INVENTION

Problems to be Solved by the Invention

For example, in order to acquire a temporal state change and the like of a biological sample by means of electrical measurement, measurements need to be made at specific time intervals. This limits the time that can be used for measurement data collection. As described above, electrical measurement of a biological sample utilizes a time-division method or a frequency-multiplexing method for improving the SNR. However, the number of measurements that can be performed during a specific period of time, and the amplitude that can be used for one measurement, are limited by the performance and/or the like of the measurement device. Such upper limit restricts improvement in an SNR.

Thus, it is a primary object of the present technology to provide a technology that enables high accuracy electrical measurement to be performed regardless of the performance and/or the like of the measurement device.

Solutions to Problems

In order to solve the foregoing problems, the present inventor has made intensive studies on technology for measuring an electrical characteristic of a biological sample, and has paid attention to the point that a same SNR are not essential for multiple frequencies depending on the purpose of measurement. Thus, the present inventor has overridden the viewpoint of the traditional technical common sense that a higher SNR is preferred, and found that use of a combination of a frequency for which the SNR is intentionally left low and a frequency for which the SNR is on the contrary improved can provide, as a result, high accuracy electrical measurement optimal for the purpose of measurement is possible. Thus, the present technology has been made.

That is, in the present technology, first, there is provided an electrical characteristic measurement apparatus, at least including:

a measurement unit that measures an electrical characteristic of a biological sample in a plurality of frequencies; and an assignment unit that performs assignment of a number of measurements and/or a measurement amplitude for each frequency.

The assignment unit can perform the assignment on the basis of one or more types of information selected from: which reagent is added to the biological sample, a measurement phase, and a trend of measurement results over time.

In addition, the assignment unit can perform the assignment of the number of measurements for each frequency such that the sum of the numbers of measurements over the plurality of frequencies is maintained within a predetermined range.

Moreover, the assignment unit can perform the assignment of the measurement amplitude for each frequency such that the amplitude resulting from superposition of the measurement amplitudes for the plurality of frequencies is maintained within a predetermined range.

The electrical characteristic measurement apparatus according to the present technology may further include: an analysis unit that analyzes a state of the biological sample on the basis of the electrical characteristic measured by the measurement unit.

Examples of the biological sample usable as a subject that is measured by the electrical characteristic measurement apparatus according to the present technology may include a blood sample.

In this case, the analysis unit may also analyze a coagulation state of the blood sample.

Next, the present technology provides an electrical characteristic measurement system including, at least, a measurement apparatus that measures an electrical characteristic of a biological sample in a plurality of frequencies, and an assignment apparatus that performs assignment of the number of measurements and/or a measurement amplitude for each frequency.

The electrical characteristic measurement system according to the present technology may further include: an analysis apparatus that analyzes a state of the biological sample on the basis of the electrical characteristic measured by the measurement apparatus.

In the electrical characteristic measurement system according to the present technology, at least some of the apparatuses may be connected to one another via a network.

In the present technology, there is further provided an electrical characteristic measurement method, at least including:

a measurement step of measuring an electrical characteristic of a biological sample in a plurality of frequencies; and an assignment step of performing assignment of a number of measurements and/or a measurement amplitude for each frequency.

In the present technology, additionally, there is provided a program used for measurement of an electrical characteristic of a biological sample in a plurality of frequencies, the program being a program for electrical characteristic measurement causing a computer to implement an assignment function that performs assignment of a number of measurements and/or a measurement amplitude for each frequency.

Effects of the Invention

The present technology enables high accuracy measurement of an electrical characteristic to be performed regardless of the performance and/or the like of the measurement device.

Note that the effects described here are not limiting, and may be any of the effects described in the present technology.

MODE FOR CARRYING OUT THE INVENTION

Figure 1:
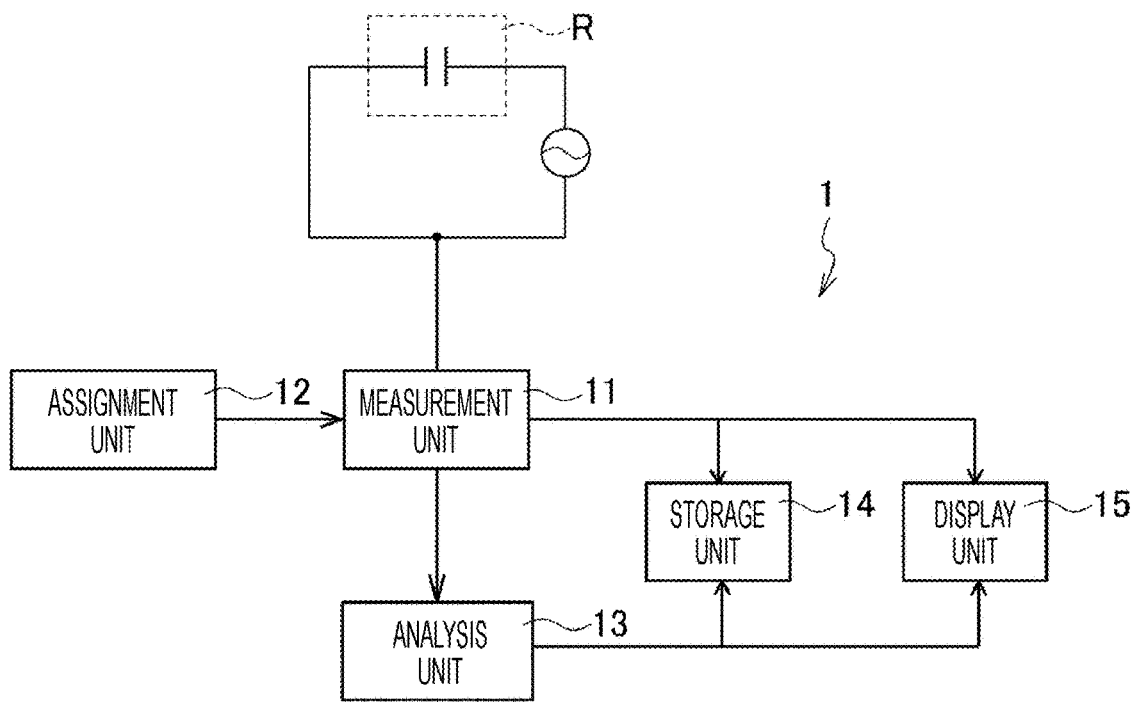
FIG. 1 is a conceptual schematic diagram schematically illustrating a concept of an electrical characteristic measurement apparatus 1 according to the present technology.

A preferred mode for practicing the present technology will be described below with reference to the drawings. Note that the embodiment described below is merely an example of typical embodiment of the present technology, and is not intended to restrict the scope of the present technology. Note that the description is provided in the order set forth below:

1. Electrical characteristic measurement apparatus 1
(1) Measurement unit 11
(2) Assignment unit 12
(3) Analysis unit 13
(4) Storage unit 14
(5) Display unit 15
(6) Biological sample
(7) Measurement flow example
2. Electrical characteristic measurement system 10
(1) Measurement apparatus 101
(2) Assignment apparatus 102

(3) Analysis apparatus 103
(4) Server 104
(5) Display apparatus 105
(6) User interface 106
3. Electrical characteristic measurement method
(1) Measurement step I
(2) Assignment step II
(3) Analysis step III
(4) Storage step IV
4. Program for electrical characteristic measurement
1. Electrical Characteristic Measurement Apparatus 1

FIG. 1 is a conceptual schematic diagram schematically illustrating a concept of an electrical characteristic measurement apparatus 1 (hereinafter also referred to as "apparatus 1") according to the present technology. The electrical characteristic measurement apparatus 1 according to the present technology includes, at least, a measurement unit 11 and an assignment unit 12; and moreover, may also include an analysis unit 13, a storage unit 14, a display unit 15, and the like as needed. Each unit will be described below in detail.

(1) Measurement Unit 11

The measurement unit 11 measures an electrical characteristic of a biological sample in multiple frequencies. In the electrical characteristic measurement apparatus 1 according to the present technology, examples of measurable electrical characteristic may include, for example, permittivity, impedance, admittance, capacitance, conductance, conductivity, phase angle, and the like. These electrical characteristics can be converted from one to another by means of the equations shown in Table 1 below. Accordingly, for example, in a case where a blood sample is used as the biological sample, an evaluation result obtained by evaluation of a hematocrit value and/or a hemoglobin content using a measurement result of permittivity is identical to an evaluation result obtained using a measurement result of impedance of the same blood sample. Many of these electrical amounts and physical property values can be described using complex numbers, which can simplify conversion equations.

TABLE 1

<Major electrical amounts and physical property values convertible from one to another>

| Electrical Amount and Physical Property Value | Symbol | Representation Using Complex Number |
|---|---|---|
| Voltage | V | $v^* = \|V\| \exp j(\omega t + \phi)$ |
| Current | I | $I^* = \|I\| \exp j(\omega t + \varphi)$ |
| Impedance | Z | $Z^* = R + jX$ (R: resistance, X: reactance) |
| Admittance | Y | $Y^* = G + jB$ (G: conductance, B: susceptance) |
| Capacitance | C | $C^* = C - jG/\omega$ |
| Conductance | G | $G^* = G + j\omega C$ |
| Loss Tangent (Dielectric Loss Tangent) | D or tan δ | |
| Loss Angle | δ | |
| Phase Angle | θ | |
| Q value | Q | |
| Permittivity | ε | $\varepsilon^* = \varepsilon - j\kappa/\omega\varepsilon_0$ |
| Conductivity | κ | $\kappa^* = \kappa + j\omega\varepsilon_0\varepsilon$ |

<Equations for relating electrical amounts and physical property values to one another>

$$Z^* = V^*/I^*$$
$$\theta = \phi - \varphi$$
$$Y^* = 1/Z^*$$
$$C = B/\omega$$
$$D = \tan\delta = G/\omega C = 1/Q$$

TABLE 1-continued $$\varepsilon^* = C^*/C_0$$
$$\kappa^* = j\omega\varepsilon_0\varepsilon^*$$

ω: Angular frequency
$\varepsilon_0$: Permittivity of vacuum (constant)
$C_0$: Constant dependent on measurement equipment etc.
Value marked with *Complex number In the measurement unit 11, the frequency band for electrical measurement may be selected as appropriate depending on the state of the biological sample to be measured, the purpose of measurement, and the like. For example, in a case where the biological sample is a blood sample, and the type of the electrical characteristic to be measured is impedance, changes are observed in the frequency bands shown in Table 2 below depending on the state change of the blood.

TABLE 2

| | Impedance | |
|---|---|---|
| State Change of Blood | Frequency with Change Observed | Frequency with Greater Change Observed |
| Blood Coagulation | 1 kHz to 50 MHz | 3 MHz to 15 MHz |
| Fibrination | 1 kHz to 50 MHz | 3 MHz to 15 MHz |
| Fibrin Clot Formation | 1 kHz to 50 MHz | 3 MHz to 15 MHz |
| Blood Clot Formation | 1 kHz to 50 MHz | 3 MHz to 15 MHz |
| Rouleau Formation of Erythrocyte | 500 kHz to 25 MHz | 2 MHz to 10 MHz |
| Blood Agglutination | 1 kHz to 50 MHz | 500 kHz to 5 MHz |
| Erythrocyte Sedimentation | 1 kHz to 50 MHz | 100 kHz to 40 MHz |
| Clot Retraction | 1 kHz to 50 MHz | 10 kHz to 100 kHz |
| Hemolysis | 1 kHz to 50 MHz | 3 MHz to 15 MHz |
| Fibrinolysis | 1 kHz to 50 MHz | 3 MHz to 15 MHz |

For example, in a case where blood coagulation is to be predicted or detected, an impedance is preferably measured in a frequency range of from 1 kHz to 50 MHz, and is more preferably measured in a frequency range of from 3 MHz to 15 MHz. Thus, setting parameters previously depending on the state of the biological sample and/or on the purpose of measurement enables a preferable frequency band as shown in Table 2 above to be automatically selected.

An example of a specific measurement method in the measurement unit 11 is as follows: a voltage having a predetermined frequency is applied to a biological sample contained in a biological sample hold unit R, and the resultant electrical characteristic obtained, such as impedance, is measured by the measurement unit 11.

As described above, the apparatus 1 may include one or multiple biological sample hold units R. This biological sample hold unit R is not essential to the electrical characteristic measurement apparatus 1, and the measurement unit 11 may be designed such that, for example, a known cartridge-type measurement container can be installed.

In a case where the apparatus 1 includes a biological sample hold unit R, the biological sample hold unit R is not particularly limited in terms of form as long as a biological sample to be measured can be contained therein, and may be designed in any form. For example, one or multiple cells may be provided on a substrate to serve as the biological sample hold unit R; or one or multiple containers may be used to serve as the biological sample hold unit R.

In a case where one or multiple containers are used as the biological sample hold unit R, such biological sample hold unit R is neither particularly limited in terms of form, and may be designed in any form, such as a circular cylinder, a polygonal cylinder having a polygonal (triangular, rectangular, or other polygonal) cross-section, a circular cone, a polygonal pyramid having a polygonal (triangular, rectangular, or other polygonal) cross-section, or a combination of one or two or more thereof, depending on the state of the biological sample and/or on the measurement method as long as the biological sample to be measured can be contained therein.

Moreover, the material(s) forming the container is/are neither particularly limited, and may be selected without limitation as long as the state of the biological sample to be measured and/or the purpose of measurement will not be affected. It is preferred in the present technology that the container be formed of a resin among others, from a viewpoint of workability and formability, and the like. The resin usable in the present technology is neither particularly limited, and one or more resins applicable for containing a biological sample may be selected without limitation and be thus used. Examples thereof include hydrophobic and electrically-insulating polymers, such as polypropylene, polymethyl methacrylate, polystyrene, acryl, polysulfone, polytetrafluoroethylene; copolymers and blended polymer mixtures thereof; and the like. It is preferred in the present technology that the biological sample hold unit be formed of one or more resins selected from polypropylene, polystyrene, acryl, and polysulfone among these. Owing to low clotting activity on blood, these resins are particularly advantageous in a case where blood is used as the biological sample.

The biological sample hold unit R is preferably configured to be sealable while the biological sample is contained therein. However, the biological sample hold unit R may not necessarily be hermetic as long as the biological sample can be held therein during a time needed for an electrical characteristic of the biological sample to be measured, and the measurement is not affected.

The specific method for introducing and hermetically enclosing a biological sample into the biological sample hold unit R is not particularly limited, and the biological sample may be introduced using any method depending on the form of the biological sample hold unit R. Examples of the method include a method in which the biological sample hold unit R is provided with a lid unit, and the lid unit is closed after introduction of the biological sample using a pipette etc. to provide sealing; a method in which an injection needle is inserted into the biological sample hold unit from the outer surface thereof, and the biological sample is then injected, after which the portion penetrated by the injection needle is filled with grease or the like to provide sealing; and the like.

The biological sample hold unit R is preferably provided with a temperature control function. An electrical characteristic, such as permittivity, of a biological sample significantly varies with a temperature change. Therefore, providing the biological sample hold unit R with a temperature control function can prevent a measurement error due to a temperature change.

The apparatus 1 may include one or multiple application units. This application unit is not essential to the electrical characteristic measurement apparatus 1, but, for example, a design that allows an electrode to be inserted into the biological sample hold unit R from the outside will enable an external application apparatus to be used.

The application unit applies a predetermined voltage to the biological sample at every measurement interval that has been set, starting at the time point when an instruction to start measurement is received, or at the time point when the electrical characteristic measurement apparatus 1 is powered on.

The number of electrodes and the material (s) forming the electrodes used as a portion of the application unit are not particularly limited, and the application unit may be configured using any number of electrodes formed of any material as long as the effects of the present technology will not be reduced. Examples of the material include titanium, aluminum, stainless steel, platinum, gold, copper, graphite, and the like. It is preferred in the present technology that the electrodes be formed of electrically conductive material including titanium among these materials. Owing to low clotting activity on blood, titanium is particularly advantageous in a case where blood is used as the biological sample.

The measurement unit 11 can measure multiple biological samples. Examples of method for measuring multiple biological samples may include, for example, a method in which a plurality of the measurement units 11 are provided to measure multiple biological samples at the same time; a method in which one measurement unit 11 is operated to scan to measure multiple biological samples; a method in which the biological sample hold unit is moved to measure multiple biological samples; a method in which a plurality of the measurement units 11 are provided, and one or multiple measurement units 11 is/are selected that actually perform(s) measurement by means of switching; and the like.

(2) Assignment Unit 12

The assignment unit 12 performs assignment of the number of measurements and/or a measurement amplitude for each frequency.

Figure 8:
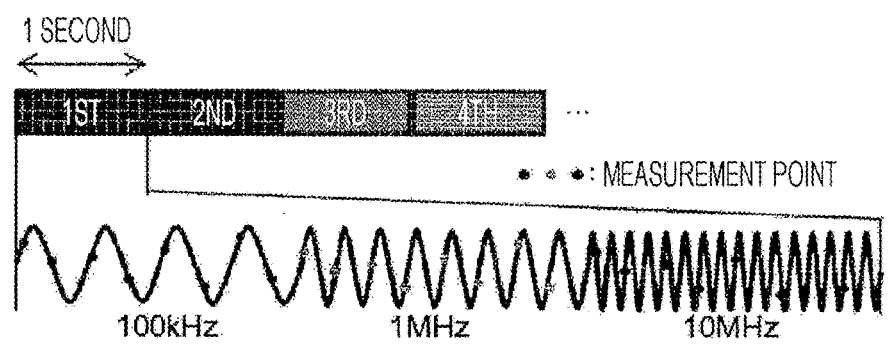
FIG. 8 is a drawing-substitute graph illustrating an example of conventional time-division method in relation to a method for measuring an electrical characteristic of a biological sample in multiple frequencies.
Figure 9:
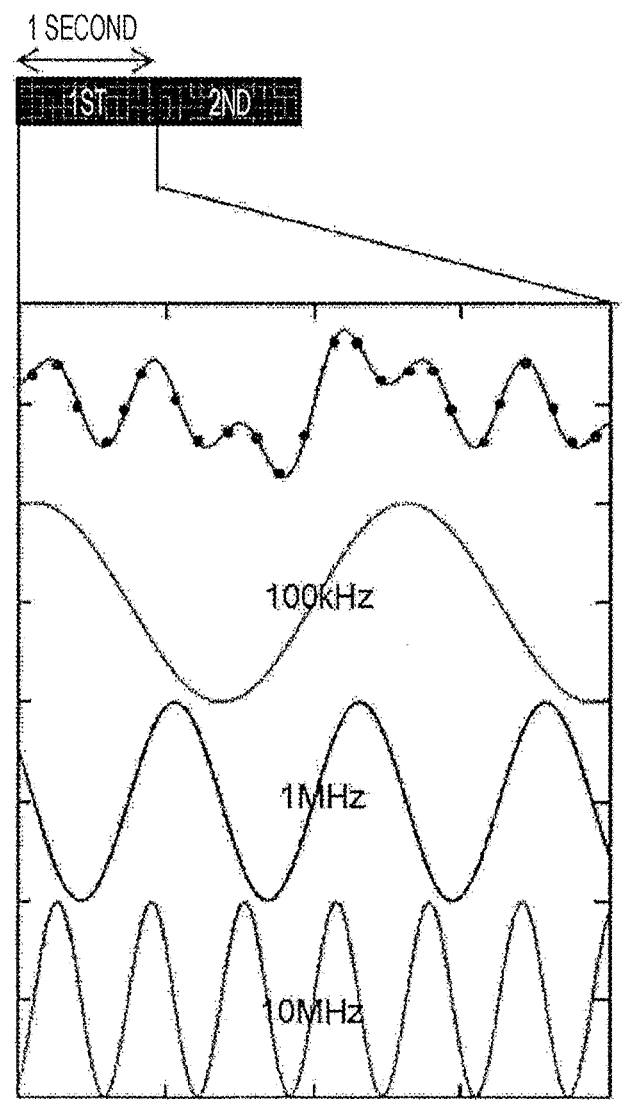
FIG. 9 is a drawing-substitute graph illustrating an example of conventional frequency-multiplexing method in relation to a method for measuring an electrical characteristic of a biological sample in multiple frequencies.

In a measurement of an electrical characteristic of a biological sample in multiple frequencies, it is a common practice for a conventional method to use a same number of measurements and a same measurement amplitude for each frequency as shown in FIGS. 8 and 9 above to constantly maintain SNRs for the respective frequencies at or above a specific value. However, when an electrical measurement is performed on a biological sample, SNRs for the respective frequencies do not necessarily need to be a same value depending on the purpose of measurement. That is, the present inventor has overridden the viewpoint of the traditional technical common sense that a higher SNR is preferable, and found that use of a combination of a frequency for which the SNR is intentionally left low and a frequency for which the SNR is on the contrary improved can provide, as a result, high accuracy electrical measurement optimal for the purpose of measurement.

For example, in a case where a blood sample is used as the biological sample, and the type of the electrical characteristic to be measured is impedance, changes are observed in different frequency bands depending on the state change of the blood as shown in Table 2 above. Therefore, for example, in a case where an impedance is measured for analysis of the degree of blood coagulation, measurement results at a frequency ranging from 1 kHz to 50 MHz are important, but measurement results at a frequency out of this range are of low importance for analysis of the degree of blood coagulation. Thus, in a case where the degree of blood coagulation is to be analyzed, lowering the SNR for frequencies out of the range of from 1 kHz to 50 MHz, or fundamentally omitting measurement at the frequencies out of the range of from 1 kHz to 50 MHz, can improve the SNR at frequencies ranging from 1 kHz to 50 MHz, and can thus improve, as a result, the analysis accuracy in an analysis of the degree of blood coagulation.

More specifically, the number of measurements that can be performed during a specific period of time, and the amplitude that can be used for one measurement, are limited by the performance and/or the like of the measurement device; and therefore, higher accuracy electrical measurement can be provided within the limits of the performance of the measurement device by assigning a higher number of measurements and/or a higher measurement amplitude for a frequency of high importance, and in contrast, assigning a lower number of measurements and/or a lower measurement amplitude for a frequency of low importance, depending on the purpose of measurement.

Figure 2:
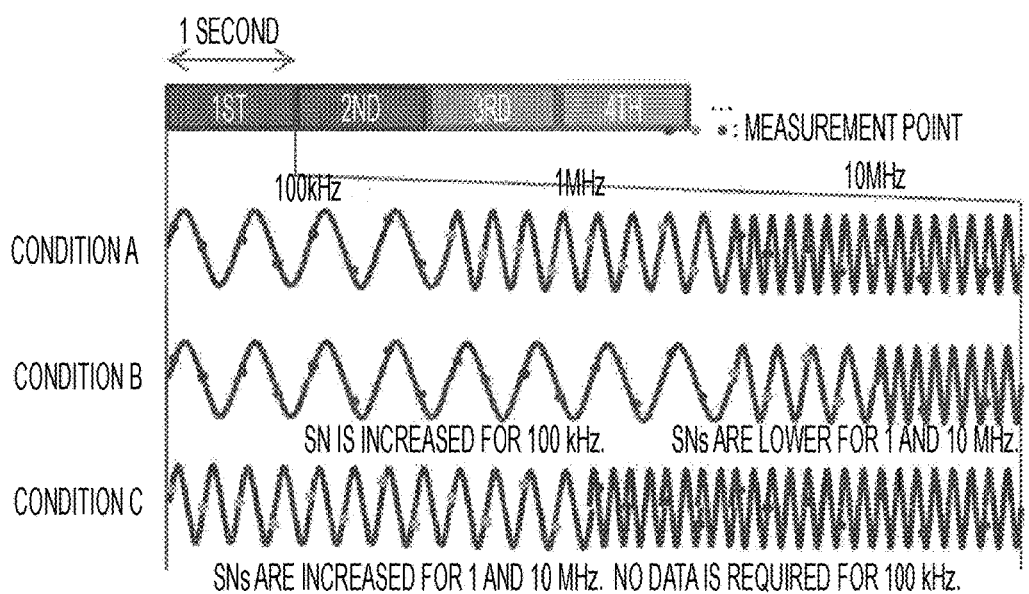
FIG. 2 is a conceptual diagram illustrating schematic pictures of waveforms of some examples in which the number of measurements is assigned by the assignment unit of the electrical characteristic measurement apparatus according to the present technology.

FIG. 2 is a conceptual diagram illustrating schematic pictures of waveforms of some examples in which the number of measurements is assigned by the assignment unit of the electrical characteristic measurement apparatus according to the present technology. Condition A provides an example in which eight measurements are assigned to each of three frequencies, which are 100 kHz, 1 MHz, and 10 MHz, and the results are averaged for each frequency to reduce noise components to obtain measurement data at each frequency. Condition B provides an example in which 16 measurements are assigned to the frequency of 100 kHz, while four measurements are assigned to each of 1 MHz and 10 MHz. Condition C provides an example in which no measurements are assigned to 100 kHz, while 12 measurements are assigned to each of 1 MHz and 10 MHz.

For example, as shown in Table 2, in a case where the degree of clot retraction is to be analyzed, measurement results at 100 kHz are more critical than measurement results at 1 MHz and 10 MHz. Thus, as shown in condition B of FIG. 2, assigning a higher number of measurements to 100 kHz can improve analysis accuracy in an analysis of the degree of clot retraction.

As described above, in the examples shown in FIG. 2, the number of measurements for each frequency is assigned such that the sum of the numbers of measurements over the multiple frequencies is maintained at 24. Thus, the assignment unit can perform assignment of the number of measurements for each frequency such that the sum of the numbers of measurements over the multiple frequencies is maintained within a predetermined range.

Figure 3:
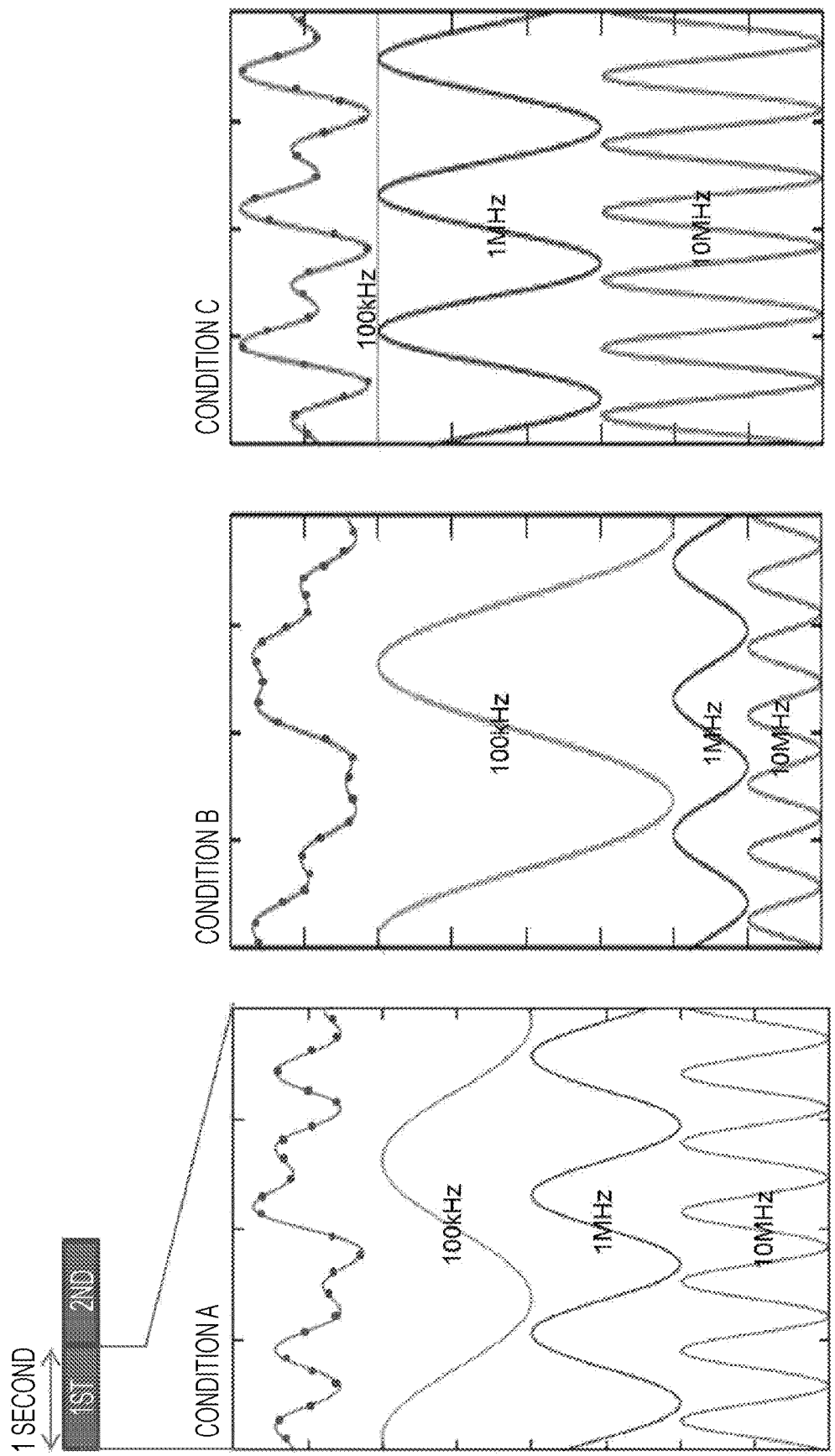
FIG. 3 is a conceptual diagram illustrating schematic pictures of waveforms of some examples in which a measurement amplitude is assigned by the assignment unit of the electrical characteristic measurement apparatus according to the present technology.

FIG. 3 is a conceptual diagram illustrating schematic pictures of waveforms of some examples in which a measurement amplitude is assigned by the assignment unit of the electrical characteristic measurement apparatus according to the present technology. Condition A provides an example in which the measurement amplitudes for the three frequencies, which are 100 kHz, 1 MHz, and 10 MHz, are equally assigned, and a synthesized signal generated therefrom is used to make the measurement. Condition B provides an example in which the measurement amplitude assigned for 100 kHz is 4 times higher than the measurement amplitude for 1 MHz and 10 MHz, and a synthesized signal generated therefrom is used to make the measurement. Condition C provides an example in which no measurements are made for 100 kHz (i.e., the amplitude is 0), the measurement amplitudes for 1 MHz and 10 MHz are equally assigned, and a synthesized signal generated therefrom is then used to make the measurement.

As described above, in the examples shown in FIG. 3, the measurement amplitude for each frequency is assigned such that the amplitude resulting from superposition of the measurement amplitudes for the respective frequencies is maintained the same. Thus, the measurement amplitude for each frequency can be assigned such that the amplitude resulting from superposition of the measurement amplitudes for the multiple frequencies is maintained within a predetermined range.

The assignment unit of the electrical characteristic measurement apparatus according to the present technology can perform the assignment on the basis of one or more types of information selected from: which reagent is added to the biological sample, a measurement phase, and a trend of measurement results over time.

For example, in a case where a reagent is added to the biological sample, a kinetic characteristic of the biological sample may vary depending on the reagent added, and the waveform obtained may thus also vary. Accordingly, the assignment unit can perform assignment of the number of measurements and/or the measurement amplitude on the basis of which reagent is added.

For example, in a case where a temporal state change etc. of the biological sample is acquired through an electrical measurement, the frequency of high importance may vary depending on the phase of the state change. For example, in a case where blood is used as the biological sample, the frequency of high importance in the rouleau phase of blood and the frequency of high importance in the blood coagulation phase differ from each other, as shown in Table 2 above. Accordingly, the assignment unit can perform assignment of the number of measurements and/or the measurement amplitude on the basis of the measurement phase.

Figure 4:
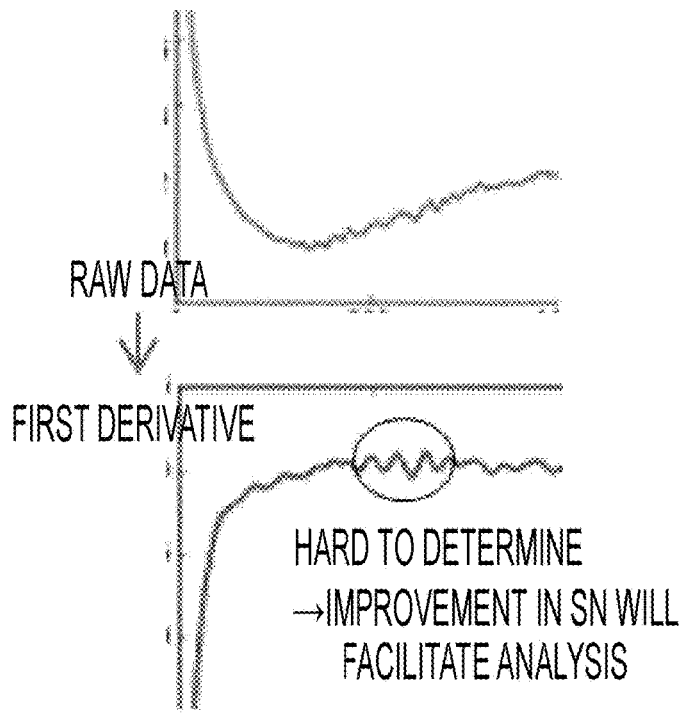
FIG. 4 is a set of drawing-substitute graphs respectively illustrating one example of raw data, and one example of first derivative data of the raw data.

In addition, in a case where a temporal state change etc. of the biological sample is acquired through an electrical measurement, the temporal trend of measurement data may vary depending on the elapsed time. For example, in a case where blood is used as the biological sample to analyze the degree of coagulation, the temporal trend of measurement data may vary such that the data stays constant before the beginning of coagulation, the data gradually changes for some time after the beginning of coagulation, then the data changes rapidly as the coagulation proceeds, and the data stays constant again once the coagulation completes. In this variation, data in a constant value period, among others, may be susceptible to noise in obtaining first derivative data therefrom (see FIG. 4). Thus, a countermeasure may be taken such that, for example, a higher number of measurements and/or a higher measurement amplitude are/is assigned for data in a constant value period, which is susceptible to noise.

Moreover, in a case where measurement data in a particular frequency band is critical in calculating a certain diagnostic value (output parameter), a higher number of measurements and/or a higher measurement amplitude may be assigned with respect to that frequency band to improve the SNR. Furthermore, in a case where a certain diagnostic value (output parameter) falls within a particular range (or is out of a particular range), a higher number of measurements and/or a higher measurement amplitude may be assigned with respect to a particular frequency to improve the SNR to further support the diagnostic result.

Note that the assignment unit can perform assignment of the number of measurements and/or the measurement amplitude on the basis of a combination of two or more conditions.

(3) Analysis Unit 13

The analysis unit 13 analyzes a biological state on the basis of an electrical characteristic of the biological sample. This analysis unit 13 is not essential to the electrical characteristic measurement apparatus 1 according to the present technology, but the state of the biological sample may also be analyzed using an external analysis apparatus or the like on the basis of the measurement result obtained by the electrical characteristic measurement apparatus 1 according to the present technology.

The state of the biological sample analyzable in the analysis unit 13 of the electrical characteristic measurement apparatus 1 according to the present technology is not particularly limited as long as a state change causes a change in the electrical characteristic of the sample, and thus various changes in the state can be analyzed and evaluated. For example, in a case where a blood sample is used as the biological sample, states changes, such as blood coagulation, fibrination, fibrin clot formation, blood clot formation, platelet aggregation, rouleau formation of erythrocyte, blood agglutination, erythrocyte sedimentation, clot retraction, hemolysis such as fibrinolysis, fibrinolysis, and the like can be analyzed and evaluated.

(4) Storage Unit 14

The electrical characteristic measurement apparatus 1 according to the present technology may include a storage unit 14 that stores the measurement results obtained by measurement in the measurement unit 11, the analysis results obtained by an analysis in the analysis unit 13, and the like. The storage unit 14 is not essential to the electrical characteristic measurement apparatus 1 according to the present technology, and it is also possible that an external storage device be connected to store the results.

In the electrical characteristic measurement apparatus 1 according to the present technology, the storage unit 14 may be individually provided in each unit, or a design may be used that allows one storage unit 14 to store various results obtained in the units.

(5) Display Unit 15

As for the display unit 15, the display unit 15 may be provided that displays a measurement result obtained by measurement in the measurement unit 11, analysis results obtained by an analysis in the analysis unit 13, and the like. The display unit 15 is not essential to the electrical characteristic measurement apparatus 1 according to the present technology, and it is also possible that an external display apparatus be connected to display results.

In the electrical characteristic measurement apparatus 1 according to the present technology, the display unit 15 may be individually provided in each unit, or a design may be used that allows one display unit 15 to display various results obtained in the units.

(6) Biological Sample

In the electrical characteristic measurement apparatus 1 according to the present technology, the measurable biological sample is not particularly limited, and may be selected without limitation as long as application of a predetermined voltage to the sample allows an electrical characteristic to be measured. In the electrical characteristic measurement apparatus 1 according to the present technology, in a measurement in which a blood sample is to be measured, may be suitably used. Specific examples of blood sample may include whole blood, a dilution thereof, a blood sample to which any of various reagents and/or a medicinal agent has been added, such as an anticoagulation-reversal agent, a coagulation activator, an anticoagulant, a platelet activator, an antiplatelet agent, and/or the like.

(7) Measurement Flow Example

Figure 5:
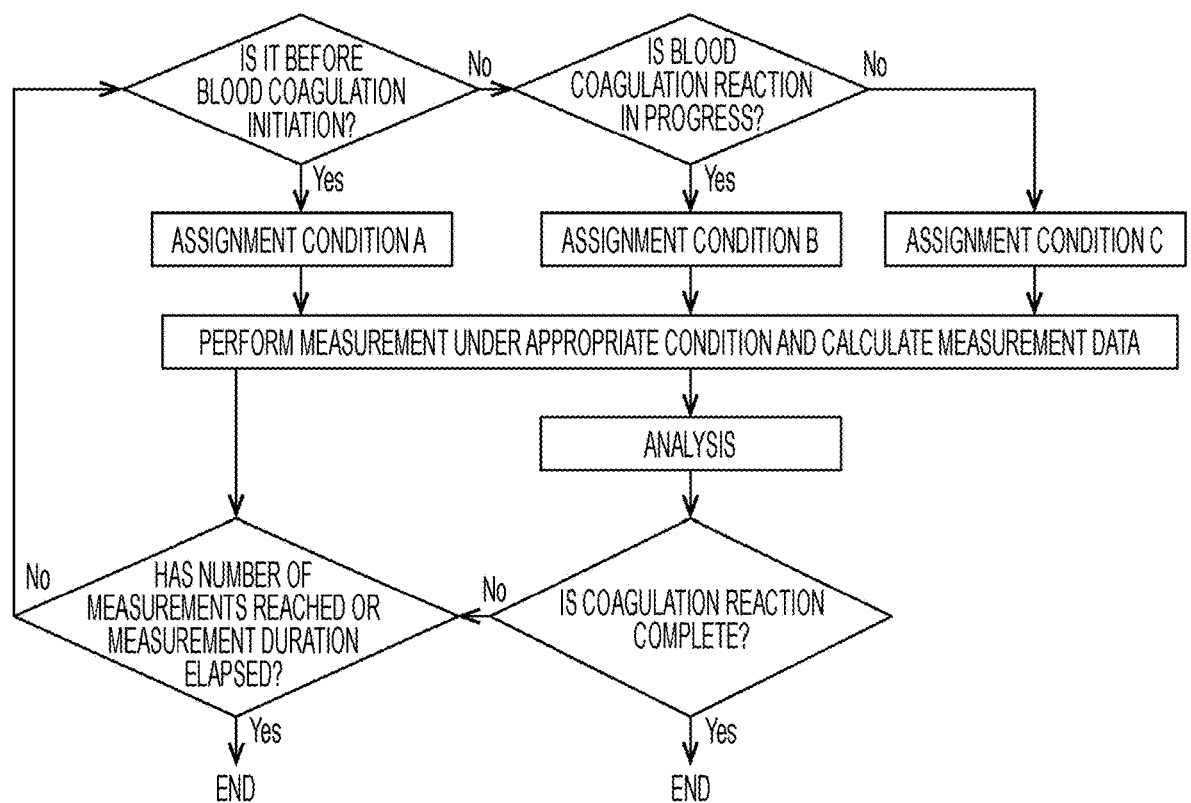
FIG. 5 is a flow diagram illustrating one example of measurement using the electrical characteristic measurement apparatus 1 according to the present technology.

FIG. 5 is a flow diagram illustrating one example of measurement using the electrical characteristic measurement apparatus 1 according to the present technology. This flow example is an example of analysis of the degree of blood coagulation using a blood sample as the biological sample.

(i) Condition Identification

First, condition identification is performed before the measurement by the measurement unit 11. In this flow example, the stage of the phase of blood coagulation is identified. Specifically, identification is performed in terms of whether it is before blood coagulation is initiated (Yes/No), whether blood coagulation reaction is in progress (Yes/No), and the like.

(ii) Assignment of Number of Measurements and/or Measurement Amplitude for Each Frequency On the basis of the result of the condition identification, the number of measurements and/or a measurement amplitude for each frequency is assigned depending on the phase. Specifically, the number of measurements and/or a measurement amplitude for each frequency can be preset for each phase, and the number of measurements and/or the measurement amplitude corresponding to the phase determined by the result of the condition identification may be automatically assigned. Alternatively, importance values for the measurement frequencies can be preset for each phase, and the number of measurements and/or a measurement amplitude for each frequency may be automatically assigned on the basis of the importance value for each measurement frequency the sum of the numbers of measurements performed in a series of measurements.

(iii) Measurement

The electrical characteristic is received that is sent from the blood sample to which a voltage is applied under the condition of the numbers of measurements and/or the measurement amplitudes for the respective frequencies that have been assigned above, and a predetermined averaging process and the like is then performed on the received raw data to calculate measurement data.

(iv) Analysis

A characteristic parameter is extracted from the measurement data, and the degree of blood coagulation is then analyzed on the basis of comparison between the parameter extracted and a reference value defining a criterion of blood coagulation.

(v) Continuation or Termination of Measurement

In a case where a preset number of measurements has not yet been reached, or a preset measurement duration has not yet elapsed (No), the measurement is further continued, while in a case where a predetermined number of measurements has been reached, or a predetermined measurement duration has elapsed (Yes), the measurement is terminated. Otherwise, in a case where further measurement is no more needed (e.g., in a case where the analysis above has shown that, for example, the blood sample has completely been coagulated), the measurement is terminated.

Note that the determination of whether or not a preset number of measurements has already been reached, or a preset measurement duration has already elapsed may be performed before the analysis, and the analysis may be made after the preset number of measurements is reached or after the preset measurement duration elapses.

2. Electrical Characteristic Measurement System 10

Figure 6:
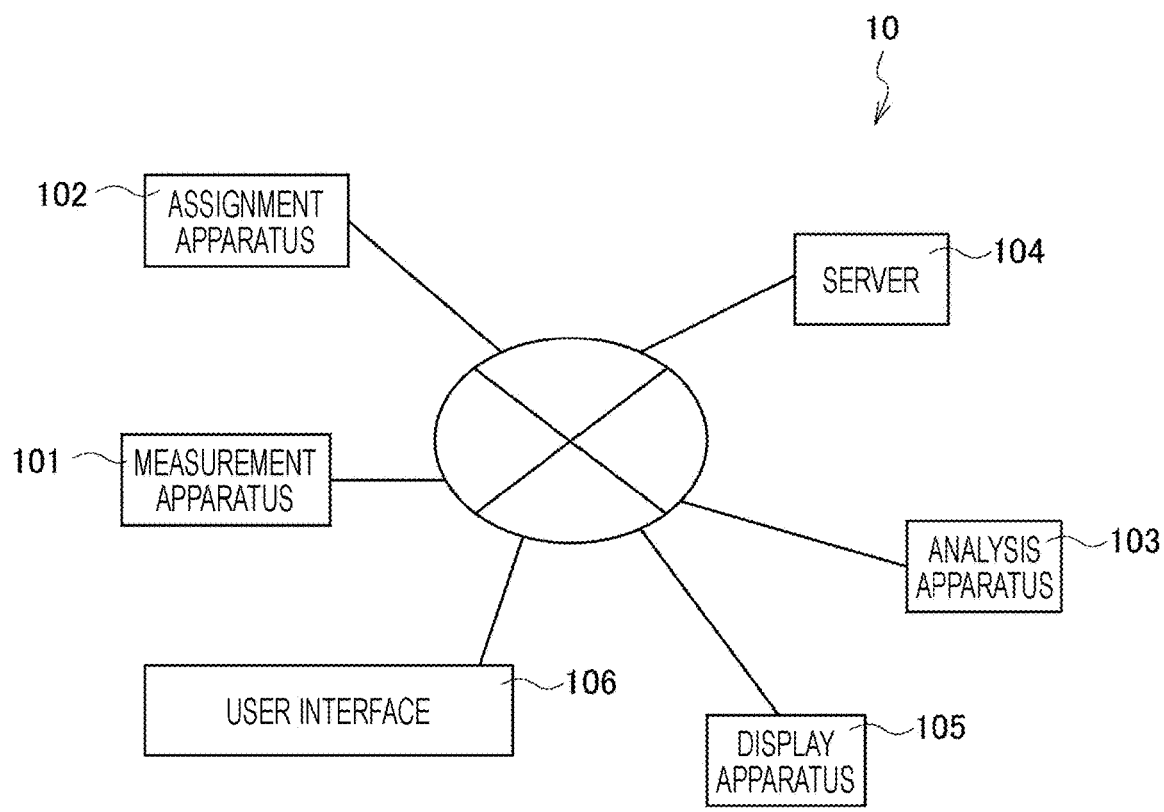
FIG. 6 is a conceptual schematic diagram schematically illustrating a concept of an electrical characteristic measurement system 10 according to the present technology.

FIG. 6 is a conceptual schematic diagram schematically illustrating a concept of an electrical characteristic measurement system 10 according to the present technology. The electrical characteristic measurement system 10 according to the present technology includes, at least, a measurement apparatus 101 and an assignment apparatus 102, in rough grouping. In addition, the electrical characteristic measurement system 10 may also include an analysis apparatus 103, a server 104, a display apparatus 105, a user interface 106, and the like as needed. Each portion will be described below in detail.

(1) Measurement Apparatus 101

The measurement apparatus 101 measures an electrical characteristic of a biological sample in multiple frequencies. Note that the details of the measurement apparatus 101 are the same as the details of the measurement unit 11 of the electrical characteristic measurement apparatus 1 described above, and therefore the explanation thereof will be omitted here.

(2) Assignment Apparatus 102

The assignment apparatus 102 performs assignment of the number of measurements and/or a measurement amplitude for each frequency. Note that the details of the assignment apparatus 102 are the same as the details of the assignment unit 12 of the electrical characteristic measurement apparatus 1 described above, and therefore the explanation thereof will be omitted here.

(3) Analysis Apparatus 103

The analysis apparatus 103 analyzes a biological state on the basis of an electrical characteristic of the biological sample. This analysis apparatus 103 is not essential to the electrical characteristic measurement system 10 according to the present technology, but the state of the biological sample may also be analyzed using an external analysis apparatus or the like on the basis of the measurement result obtained by the electrical characteristic measurement system 10 according to the present technology. Note that the details of the analysis apparatus 103 are the same as the details of the analysis unit 13 of the electrical characteristic measurement apparatus 1 described above, and therefore the explanation thereof will be omitted here.

(4) Server 104

The server 104 can store the results of measurement performed in the measurement apparatus 101, the results of analysis performed in the analysis apparatus 103, and/or the like. This server is not essential to the electrical characteristic measurement system 10 according to the present technology, but the measurement results obtained in the measurement apparatus 101, the analysis results obtained in the analysis apparatus 103, and/or the like, of the electrical characteristic measurement system 10 according to the present technology may also be stored using an external server or the like. Note that the details of the server 104 are the same as the details of the storage unit 14 of the electrical characteristic measurement apparatus 1 described above, and therefore the explanation thereof will be omitted here.

(5) Display Apparatus 105

As for the display apparatus 105, the display apparatus 105 may be provided that displays a measurement result obtained by measurement in the measurement apparatus 101, analysis results obtained by an analysis in the analysis apparatus 103, and the like. The display apparatus 105 is not essential to the electrical characteristic measurement system 10 according to the present technology, and it is also possible that an external display apparatus be connected to display results. Note that the details of the display apparatus 105 are the same as the details of the display unit 15 of the electrical characteristic measurement apparatus 1 described above, and therefore the explanation thereof will be omitted here.

(6) User Interface 106

The user interface 106 is a unit for being operated by a user. Through the user interface 106, a user can access each portion of the electrical characteristic measurement system 10 according to the present technology.

In the electrical characteristic measurement system 10 according to the present technology described above, the measurement apparatus 101, the assignment apparatus 102, the analysis apparatus 103, the server 104, the display apparatus 105, and the user interface 106 may be connected to one another via a network.

3. Electrical Characteristic Measurement Method

Figure 7:
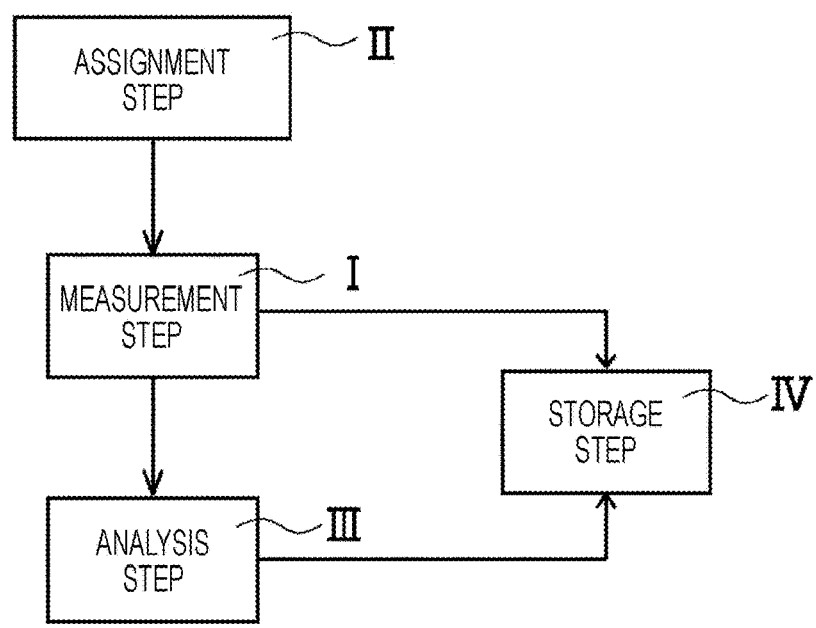
FIG. 7 is a flowchart of an electrical characteristic measurement method according to the present technology.

FIG. 7 is a flowchart of an electrical characteristic measurement method according to the present technology. The electrical characteristic measurement method according to the present technology is a method that performs a measurement step I and an assignment step II. In addition, an analysis step III, a storage step IV, and the like may also be performed as needed. Note that the details of each step are the same as the details of the corresponding one of the measurement unit 11, the assignment unit 12, the analysis unit 13, and the storage unit 14, of the electrical characteristic measurement apparatus 1 described above, and therefore the explanation thereof will be omitted here.

4. Program for Electrical Characteristic Measurement

The program for electrical characteristic measurement according to the present technology is a program for use in measuring an electrical characteristic of a biological sample in multiple frequencies, and is a program for electrical characteristic measurement for causing a computer to implement an assignment function that performs assignment of the number of measurements and/or a measurement amplitude for each frequency. The program for electrical characteristic measurement may also cause a computer to implement an analysis function, a storage function, and the like as needed.

In other words, the program for electrical characteristic measurement according to the present technology is a program for causing a computer to implement the electrical characteristic measurement method according to the present technology described above. Thus, the details of each function are the same as the details of the corresponding one of the steps of the electrical characteristic measurement method described above, and therefore the explanation thereof will be omitted here.

Note that the present technology can also have the configurations described below.

(1)

An electrical characteristic measurement apparatus, at least including:

a measurement unit that measures an electrical characteristic of a biological sample in a plurality of frequencies; and an assignment unit that performs assignment of a number of measurements and/or a measurement amplitude for each frequency.

(2)

The electrical characteristic measurement apparatus according to (1), in which the assignment unit performs the assignment on the basis of one or more types of information selected from: which reagent is added to the biological sample, a measurement phase, and a trend of measurement results over time.

(3)

The electrical characteristic measurement apparatus according to (1) or (2), in which the assignment unit performs the assignment of the number of measurements for each frequency such that a sum of the numbers of measurements over the plurality of frequencies is maintained within a predetermined range.

(4)

The electrical characteristic measurement apparatus according to any one of (1) to (3), in which the assignment unit performs the assignment of the measurement amplitude for each frequency such that an amplitude resulting from superposition of the measurement amplitudes for the plurality of frequencies is maintained within a predetermined range.

(5)

The electrical characteristic measurement apparatus according to any one of (1) to (4), further including:

an analysis unit that analyzes a state of the biological sample on the basis of the electrical characteristic measured by the measurement unit.

(6)

The electrical characteristic measurement apparatus according to anyone of (1) to (5), in which the biological sample is a blood sample.

(7)

The electrical characteristic measurement apparatus according to (6), in which the biological sample is a blood sample, and the analysis unit analyzes a coagulation state of the blood sample.

(8)

An electrical characteristic measurement system, at least including:

a measurement apparatus that measures an electrical characteristic of a biological sample in a plurality of frequencies; and an assignment apparatus that performs assignment of a measurement interval and/or a measurement amplitude for each frequency.

(9)

The electrical characteristic measurement system according to (8), further including:

an analysis apparatus that analyzes a state of the biological sample on the basis of the electrical characteristic measured by the measurement apparatus.

(10)

The electrical characteristic measurement system according to (8) or (9), in which at least some of the apparatuses may be connected to one another via a network.

(11)

An electrical characteristic measurement method, at least including:

a measurement step of measuring an electrical characteristic of a biological sample in a plurality of frequencies; and an assignment step of performing assignment of a number of measurements and/or a measurement amplitude for each frequency.

(12)

A program used for measurement of an electrical characteristic of a biological sample in a plurality of frequencies, the program being a program for electrical characteristic measurement causing a computer to implement an assignment function that performs assignment of a number of measurements and/or a measurement amplitude for each frequency.

REFERENCE SIGNS LIST

1 Electrical characteristic measurement apparatus
11 Measurement unit
12 Assignment unit
13 Analysis unit
14 Storage unit
15 Display unit
10 Electrical characteristic measurement system
101 Measurement apparatus
102 Assignment apparatus
103 Analysis apparatus
104 Server
105 Display apparatus
106 User interface
I Measurement step
II Assignment step
III Analysis step
IV Storage step

The invention claimed is:

1. An electrical characteristic measurement apparatus, comprising:

a measurement unit that measures an electrical characteristic of a biological sample in a plurality of frequencies; and an assignment unit that performs assignment of a number of measurements and a measurement amplitude for each frequency, wherein the assignment unit is configured to assign a first amplitude and a first frequency of the plurality of frequencies to a first electrical signal and a second amplitude and a second frequency of the plurality of frequencies, different from the first amplitude and the first frequency, to a second electrical signal and wherein the measurement unit is configured to apply to the biological sample a synthesized electrical signal generated by superimposing the first electrical signal and the second electrical signal.

2. The electrical characteristic measurement apparatus according to claim 1, wherein the assignment unit performs the assignment on the basis of one or more types of information selected from: which reagent is added to the biological sample, a condition of the biological sample, and a trend of measurement results over time.

3. The electrical characteristic measurement apparatus according to claim 1, wherein the assignment unit performs the assignment of the number of measurements for each frequency such that a sum of the numbers of measurements over the plurality of frequencies is maintained within a predetermined range.

4. The electrical characteristic measurement apparatus according to claim 1, wherein the assignment unit performs the assignment of the measurement amplitude for each frequency such that an amplitude resulting from superposition of the measurement amplitudes for the plurality of frequencies is maintained within a predetermined range.

5. The electrical characteristic measurement apparatus according to claim 1, further comprising:

an analysis unit that analyzes the biological sample on the basis of the electrical characteristic measured by the measurement unit.

6. The electrical characteristic measurement apparatus according to claim 5, wherein the biological sample is a blood sample, and the analysis unit analyzes a coagulation state of the blood sample.

7. The electrical characteristic measurement apparatus according to claim 1, wherein the biological sample is a blood sample.

8. An electrical characteristic measurement system, comprising:

a measurement apparatus that measures an electrical characteristic of a biological sample in a plurality of frequencies; and an assignment apparatus that performs assignment of a number of a measurement period and a measurement amplitude for each frequency, wherein the assignment apparatus is configured to assign a first amplitude and a first frequency of the plurality of frequencies to a first electrical signal and a second amplitude and a second frequency of the plurality of frequencies, different from the first amplitude and the first frequency, to a second electrical signal and wherein the measurement apparatus is configured to apply to the biological sample a synthesized electrical signal generated by superimposing the first electrical signal and the second electrical signal.

9. The electrical characteristic measurement system according to claim 8, further comprising:
an analysis apparatus that analyzes the biological sample on the basis of the electrical characteristic measured by the measurement apparatus.

10. The electrical characteristic measurement system according to claim 8, wherein at least some of the apparatuses are connected to one another via a network.

11. An electrical characteristic measurement method, comprising:
measuring an electrical characteristic of a biological sample in a plurality of frequencies; and performing assignment of a number of measurements and a measurement amplitude for each frequency, wherein performing assignment includes assigning a first amplitude and a first frequency of the plurality of frequencies to a first electrical signal and a second amplitude and a second frequency of the plurality of frequencies, different from the first amplitude and the first frequency, to a second electrical signal and wherein measuring includes applying to the biological sample a synthesized electrical signal generated by superimposing the first electrical signal and the second electrical signal.

12. A non-transitory computer-readable medium containing instructions that, when executed by a processing device, perform an electrical characteristic measurement method comprising:
measuring an electrical characteristic of a biological sample in a plurality of frequencies; and
performing assignment of a number of measurements and a measurement amplitude for each frequency, wherein performing assignment includes assigning a first amplitude and a first frequency of the plurality of frequencies to a first electrical signal and a second amplitude and a second frequency of the plurality of frequencies, different from the first amplitude and the first frequency, to a second electrical signal and wherein measuring includes applying to the biological sample a synthesized electrical signal generated by superimposing the first electrical signal and the second electrical signal.

\* \* \* \* \*